US012569623B2

(12) United States Patent
Cho et al.

(10) Patent No.: US 12,569,623 B2
(45) Date of Patent: Mar. 10, 2026

(54) DRUG INJECTION CONTROL DEVICE HAVING STABLE OPERATION STRUCTURE OF INJECTION BUTTON THROUGH BUTTON PLATE POSITIONED IN DOSE DIAL

(71) Applicant: POONGLIM PHARMATECH INC., Jeollabuk-do (KR)

(72) Inventors: Hee Min Cho, Jeollabuk-do (KR); Jong Deok Yun, Jeollabuk-do (KR); Jae Cheon Kim, Jeollabuk-do (KR); Ki Yoon Kang, Jeollabuk-do (KR); Hyeong Chan Son, Jeollabuk-do (KR); Seon Hye Yoon, Jeollabuk-do (KR)

(73) Assignee: POONGLIM PHARMATECH INC., Jeollabuk-do (KR)

( * ) Notice: Subject to any disclaimer, the term of this patent is extended or adjusted under 35 U.S.C. 154(b) by 811 days.

(21) Appl. No.: 17/795,645

(22) PCT Filed: Nov. 2, 2021

(86) PCT No.: PCT/KR2021/015681
§ 371 (c)(1),
(2) Date: Jul. 27, 2022

(87) PCT Pub. No.: WO2022/098046
PCT Pub. Date: May 12, 2022

(65) Prior Publication Data
US 2023/0074677 A1     Mar. 9, 2023

(30) Foreign Application Priority Data
Nov. 3, 2020    (KR) ........................ 10-2020-0145237

(51) Int. Cl.
*A61M 5/31*          (2006.01)
*A61M 5/315*        (2006.01)

(52) U.S. Cl.
CPC ...... *A61M 5/3158* (2013.01); *A61M 5/31515* (2013.01)

(58) Field of Classification Search
CPC .................................................. A61M 5/3158
See application file for complete search history.

(56) References Cited

U.S. PATENT DOCUMENTS 12,415,035 B2 *   9/2025   Cho .................. A61M 5/31543
12,427,263 B2 *   9/2025   Cho .................. A61M 5/31543

FOREIGN PATENT DOCUMENTS

KR      10-2007-0065878 A      6/2007
KR           10-2224582 B1      3/2021
(Continued)

OTHER PUBLICATIONS

International Search Report for PCT/KR2021/015681 mailed on Feb. 18, 2022.

*Primary Examiner* — William R Carpenter
(74) *Attorney, Agent, or Firm* — The PL Law Group, PLLC

(57)          ABSTRACT

A drug injection control device has a structure in which a rod lock screw-coupled to an outer circumferential surface of a piston rod can only make a linear motion under restricted rotation in a rod holder with the rotation of a rod guide and the sub-linear motion of the piston rod. When an injection amount of drug is preset through an injection amount setting module configured to make a rotational motion with a dose dial in a housing to set the amount of drug to be injected by storing the twisting moment in a torsion spring, a button plate is fixed and positioned in the dose dial to perform a function of supporting a button spring, and an injection button is slidably coupled through the button plate, so the (Continued)

injection button rotates simultaneously with the rotation of the dose dial, but allows a stable pushing operation through the button plate.

7 Claims, 9 Drawing Sheets

(56)                    References Cited

FOREIGN PATENT DOCUMENTS

| | | | |
|---|---|---|---|
| WO | WO 99/38554 A1 | 8/1999 | |
| WO | WO 2011/089246 A1 | 7/2011 | |
| WO | WO 2014/161952 A1 | 10/2014 | |
| WO | WO 2015/032780 A1 | 3/2015 | |
| WO | WO 2016/055620 A1 | 4/2016 | |
| WO | WO 2017/220311 A1 | 12/2017 | |
| WO | WO-2019057916 A1 * | 3/2019 | .......... A61M 5/2033 |

* cited by examiner

FIG. 3

DRUG INJECTION CONTROL DEVICE HAVING STABLE OPERATION STRUCTURE OF INJECTION BUTTON THROUGH BUTTON PLATE POSITIONED IN DOSE DIAL

PRIORITY

This application claims benefit under 35 U.S.C. 119, 120, 121, or 365(c), and is a National Stage entry from International Application No. PCT/KR2021/015681, filed Nov. 2, 2021, which claims priority to the benefit of Korean Patent Application No. 10-2020-0145237 filed in the Korean Intellectual Property Office on Nov. 3, 2020, the entire contents of which are incorporated herein by reference.

BACKGROUND

1. Technical Field

The present disclosure relates to a drug injection control device in which a button plate coupled to an injection button is positioned in a dose dial to allow a stable operation of the injection button which makes a linear motion in the dose dial.

2. Background Art

Autoinjectors are devices for easy self-administration by patients or even untrained personnel, and shield the patients from being exposed to syringe needles. There is a need for autoinjectors that are easy to use, acceptably small in size and simple to improve the manufacturing, assembly and use, resulting in reduced manufacturing and assembly costs, and have the minimized influence on the environment.

Drug injectors used for subcutaneous injection require highly specialized skills and experience to use them, and recently, automatic drug injectors have been proposed, in which drugs are automatically injected via syringe needles that penetrate into the skin when pressed against the skin.

Among the commercially available syringes for drug injection, pen-type syringes have functionality to feed multiple doses from drug containers, and the dose quantity is set immediately before the dose delivery. Since most of drug delivery device users have little experience, in some instances, it is desirable to provide the users with some types of indicators or information notifying that the dose delivery sequences were carried out and it is safe to remove the drug delivery devices from the dose delivery sites.

Korean Patent Publication No. 10-2017-00065623 discloses a drug injector device including a housing having an internal space and a lengthwise window, a rotatable dose dial that is maintained in the axial direction with respect to the housing, and a rotatable scale drum to present an indication for displaying the size of the set dose, wherein a sliding element of the scale drum is configured to slide in the axial direction with respect to the housing during the dose setting, the indication presented by the scale drum can be seen through a sliding window and accordingly the lengthwise window and the sliding window are combined with the indication to form a dose size display, the rotatable scale drum is rotated in the internal space formed by the housing during the dose setting, and an inner surface of the sliding element has inner features coupled to outer screw threads on an outer surface of the scale drum.

Korean Patent Publication No. 10-2019-0017806 discloses a drug injection device, and more particularly, a drug delivery device including a housing and an actuation mechanism arranged inside the housing, wherein the actuation mechanism includes a plunger rod arranged to act on a stopper of a drug container and an actuator arranged slidable and connected to the plunger rod for acting on the stopper when the actuator is operated by displacing it in a longitudinal direction of the actuation mechanism.

SUMMARY

The present disclosure is designed to solve the above-described problem of the conventional technology, and therefore the present disclosure is directed to providing a drug injection control device technology in which a button plate coupled to an injection button is positioned in a dose dial to allow a stable operation of the injection button which makes a linear motion in the dose dial when setting the drug dose through the dose dial and injecting the set drug through the injection button.

To achieve the above-described object, a drug injection control device according to the present disclosure includes a hollow housing 10, a dose dial 20 rotatably coupled to a side of the housing 10, a cartridge holder 30 fixedly coupled to an opposite side of the housing 10 wherein a cartridge containing a drug is received in the cartridge holder 30 and an injection needle is coupled to a side to deliver the drug, an injection button 40 positioned on an outer side of the dose dial 20 and a cap 60 separably coupled to an outside of the cartridge holder 30, and includes an injection amount setting module 100 to set an amount of the drug to be injected by storing a twisting moment in a torsion spring 140 positioned in the housing 10; and a drug delivery module 200 to deliver the drug from the cartridge embedded in the cartridge holder 30 by moving through the release of the twisting moment applied to the torsion spring 140, and preferably, the injection amount setting module 100 may include a button plate 160 fixed and positioned in the dose dial 20 to perform a function of supporting the button spring 50, the injection button 40 may be slidably coupled through the button plate 160, the drug delivery module 200 may include a rod guide 210 switchably coupled to the injection amount setting module 100 by the operation of the injection button 40, and a piston rod 220 screw-coupled to an outer side of the rod guide 210 to deliver the drug from the cartridge embedded in the cartridge holder 30 by making a linear motion with a rotational motion of the rod guide 210, and the injection button 40 may rotate simultaneously with the rotation of the dose dial 20, but may allow a stable pushing motion through the button plate 160.

Preferably, the button plate 160 may be fixed to a plate fixing step 24 formed along a circumferential direction on an inner surface of the dose dial 20 on a first dial chamber formed through a partition wall in the dose dial 20.

Preferably, the injection amount setting module 100 may include a reset tube 110 switchably coupled to the dose dial 20 by the operation of the injection button 40, a ratchet tube 120 coupled to an outer side of the reset tube 110 to rotate at the same time, a scale drum 130 which slidably rotates along an axial direction on an outer surface of the ratchet tube 120, and a torsion spring 140 having two ends coupled to the housing 10 and the ratchet tube 120, and the rod guide 210 coupled to the reset tube 110 may be connected to an inside of the piston rod 220 by screw rotation coupling to allow a sub-linear motion of the piston rod 220 through the rotation of the rod guide 210, thereby having a cartridge drug release structure through the screw coupling between the piston rod 220 and the rod guide 210.

Preferably, the drug injection control device may include a spring base 150 coupled to the housing 10, the torsion spring 140 may have two ends coupled to the spring base 150 and the ratchet tube 120, respectively, and during the rotation through the dose dial 20, a side of the torsion spring 140 fixed to the ratchet tube 120 may rotate, while an opposite side of the torsion spring 140 fixed to the spring base 150 may be kept in fixed state, to get the spring twisted.

Preferably, the rod guide 210 may include a guide body having a guide spiral protrusion separably coupled to a guide coupling groove formed in an inner surface of the piston rod 220, and a guide rotation protrusion protruding on an outer surface of one side of the guide body and separably coupled to a guide coupling groove formed on an inner surface of the reset tube 110.

In the drug injection control device according to the present disclosure as described above, when the injection amount of drug is preset according to the user's intention through the injection amount setting module configured to make a rotational motion with the dose dial in the housing to set the amount of drug to be injected by storing the twisting moment in the torsion spring, the button plate is fixed and positioned in the dose dial to perform the function of supporting the button spring, and the injection button is slidably coupled through the button plate, so the injection button rotates simultaneously with the rotation of the dose dial, but allows a stable pushing operation through the button plate.

Additionally, the rod guide is connected to the inside of the piston rod by screw rotation coupling through the reset tube movably coupled to the injection button to allow a sub-linear motion of the piston rod through the rotation of the rod guide, thereby having a stable cartridge drug release structure through the screw coupling between the piston rod and the rod guide.

BRIEF DESCRIPTION OF THE DRAWINGS

Figure 3:
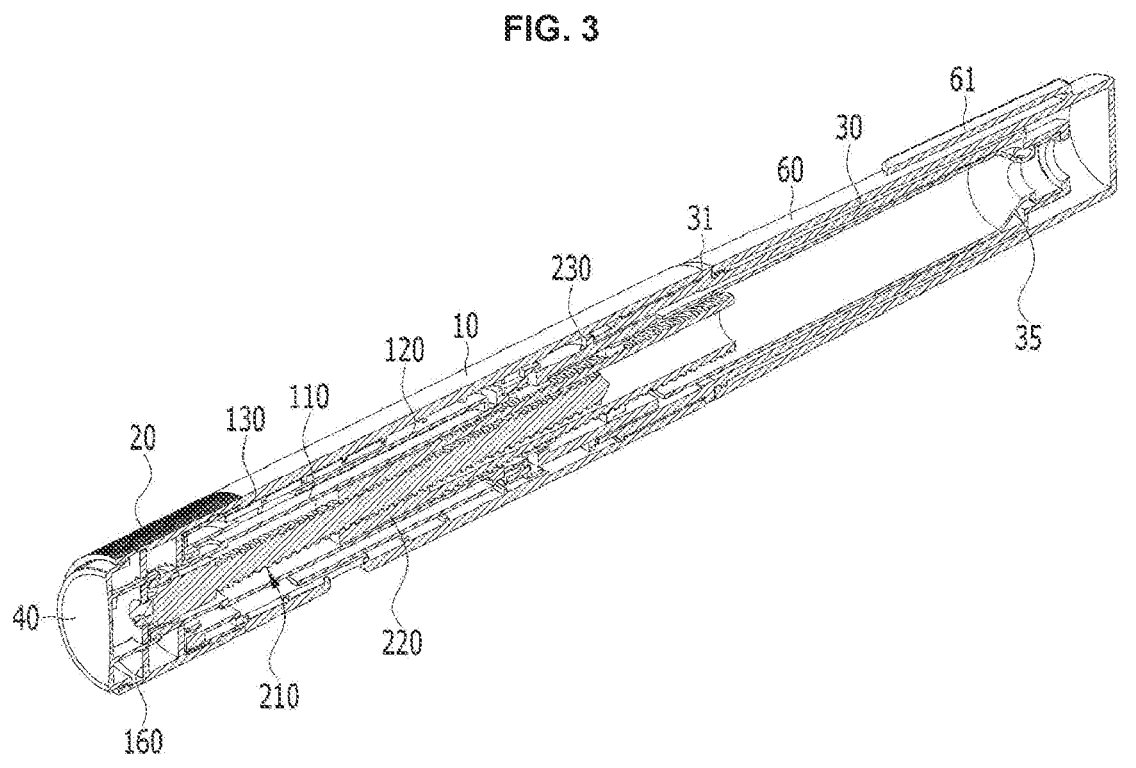

FIG. 3 is a cross-sectional view of the drug injection control device of FIG. 1.

DETAILED DESCRIPTION

Figure 1:
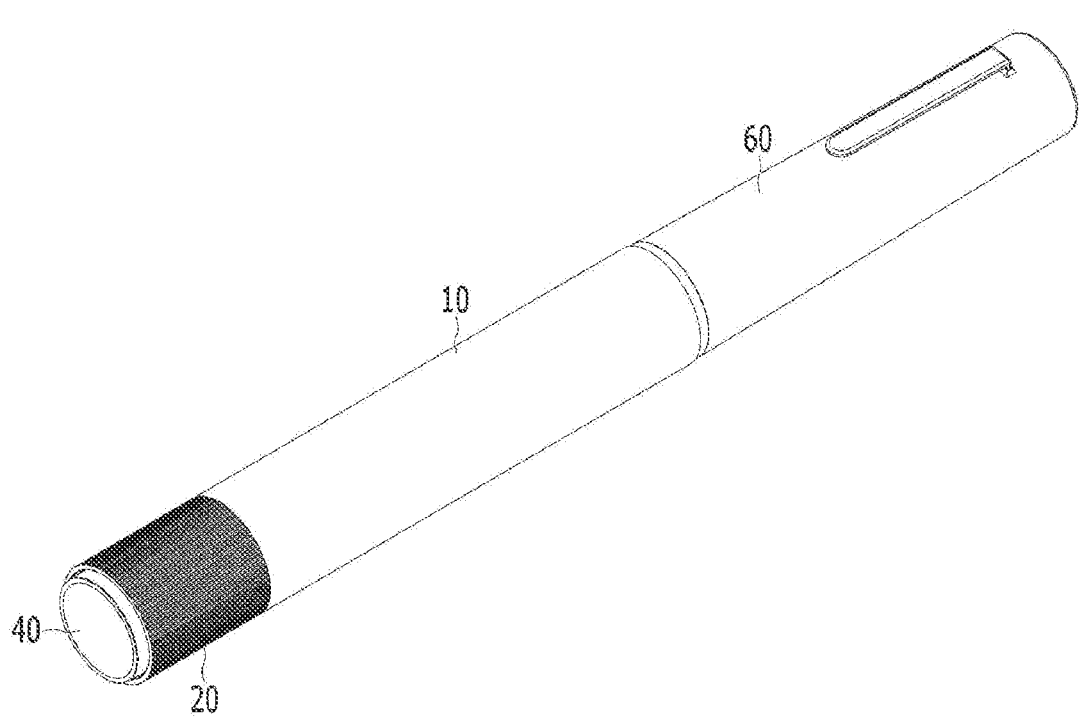
FIG. 1 is an assembled perspective view of a drug injection control device according to an embodiment of the present disclosure.
Figure 2:
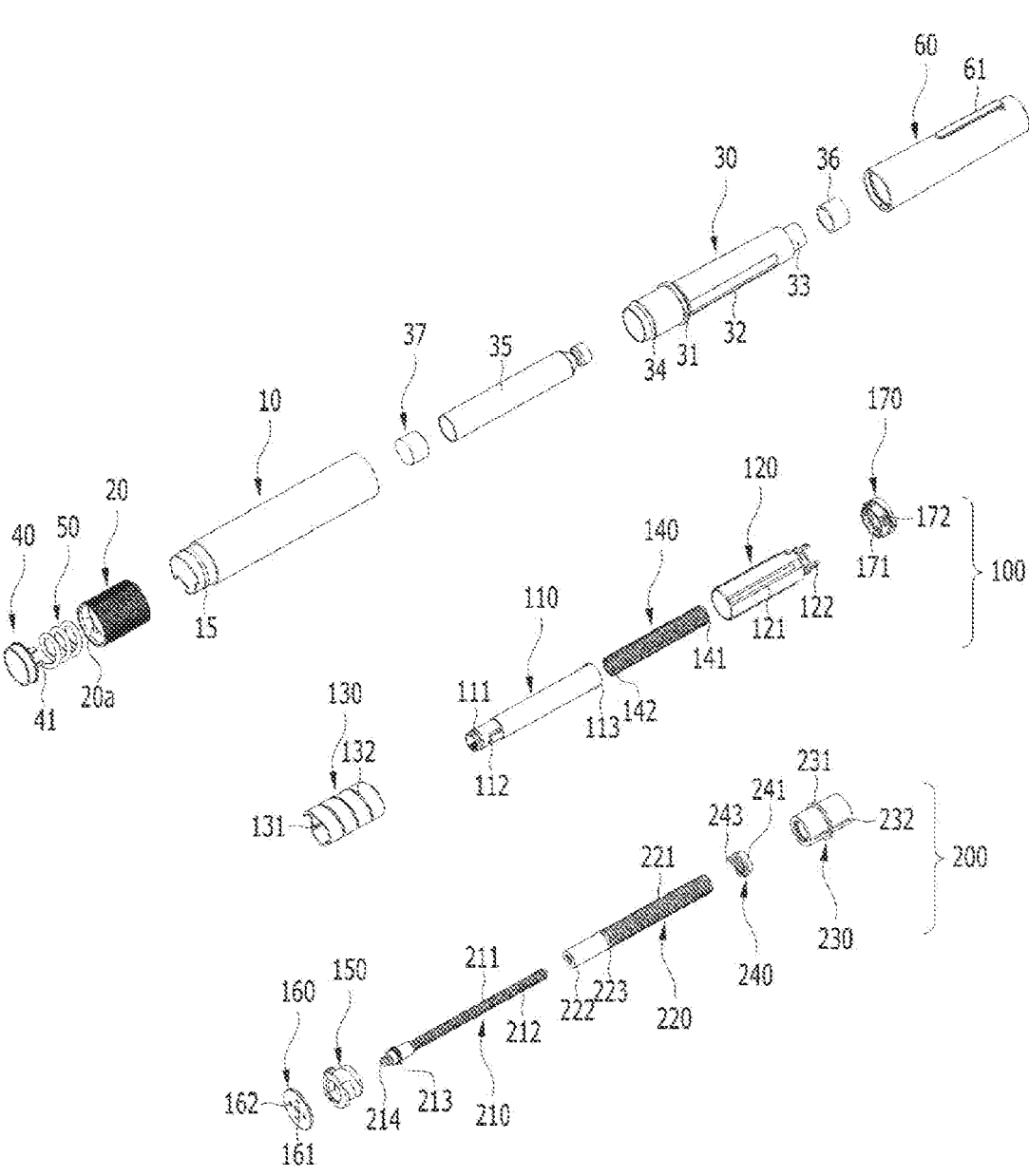
FIG. 2 is an exploded perspective view of the drug injection control device according to FIG. 1.
Figure 4:
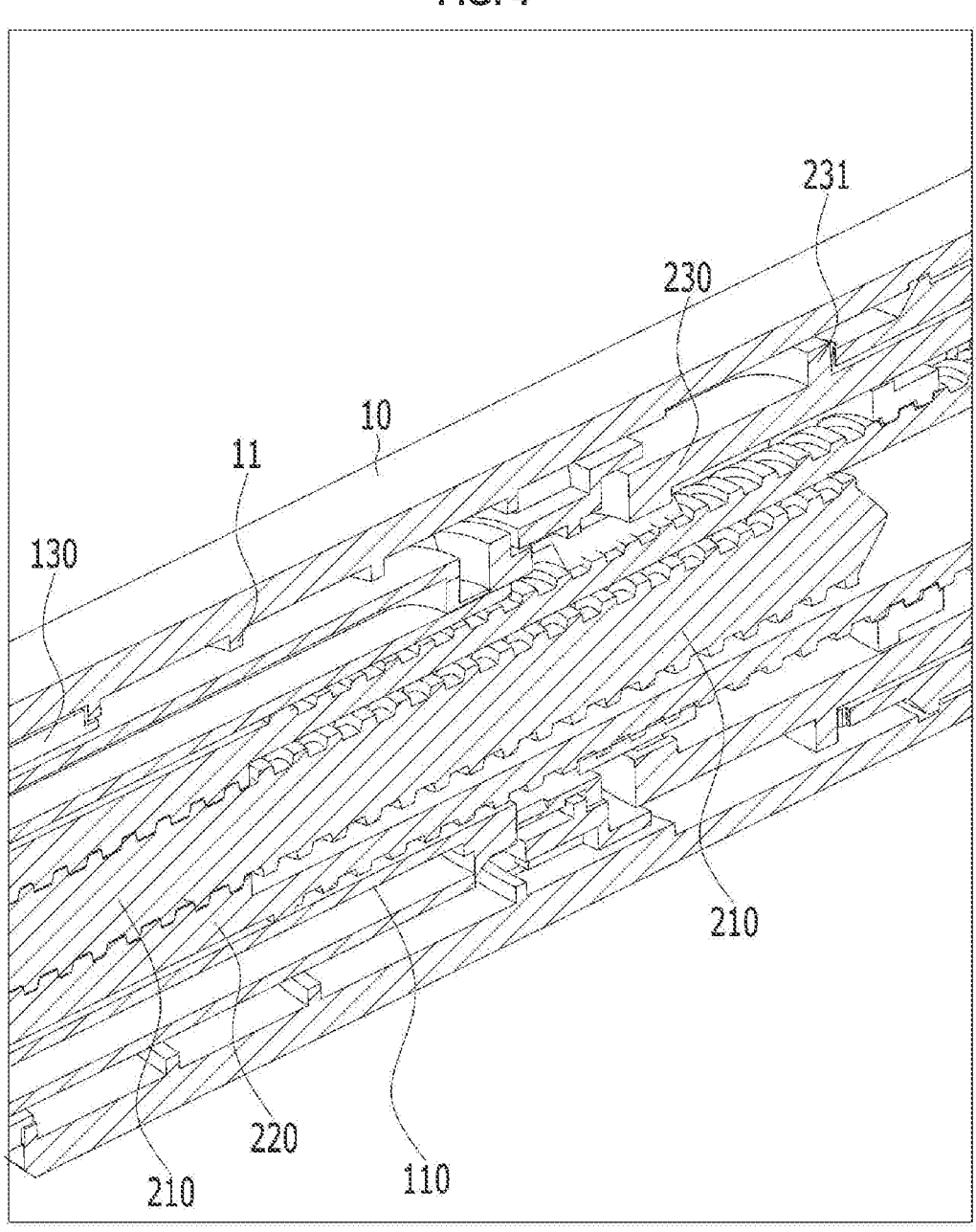
FIG. 4 is an enlarged view of section A in FIG. 3.
Figure 5:
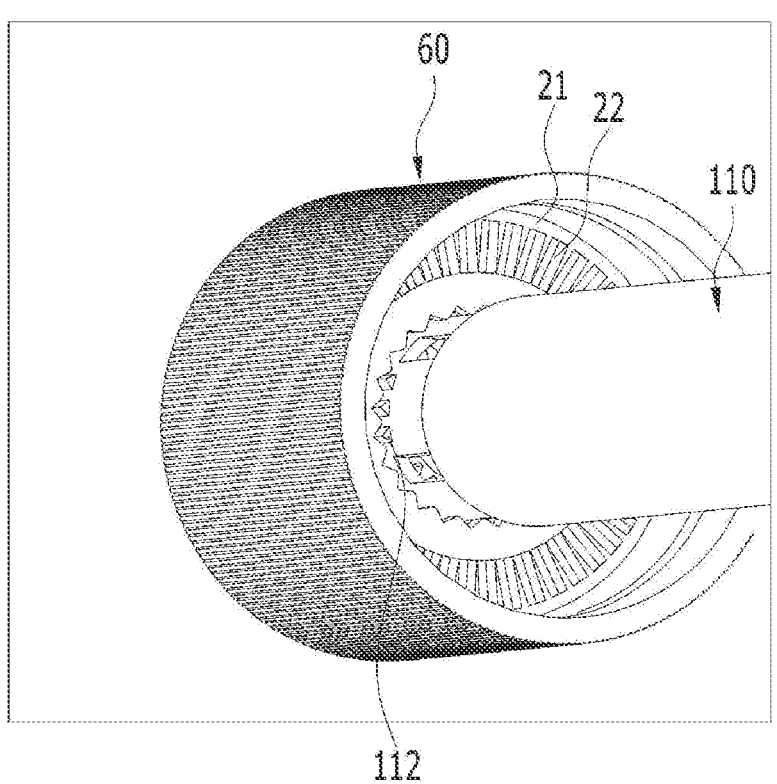
FIG. 5 is a diagram showing a connection relationship between a dose dial and a reset tube.
Figure 6:
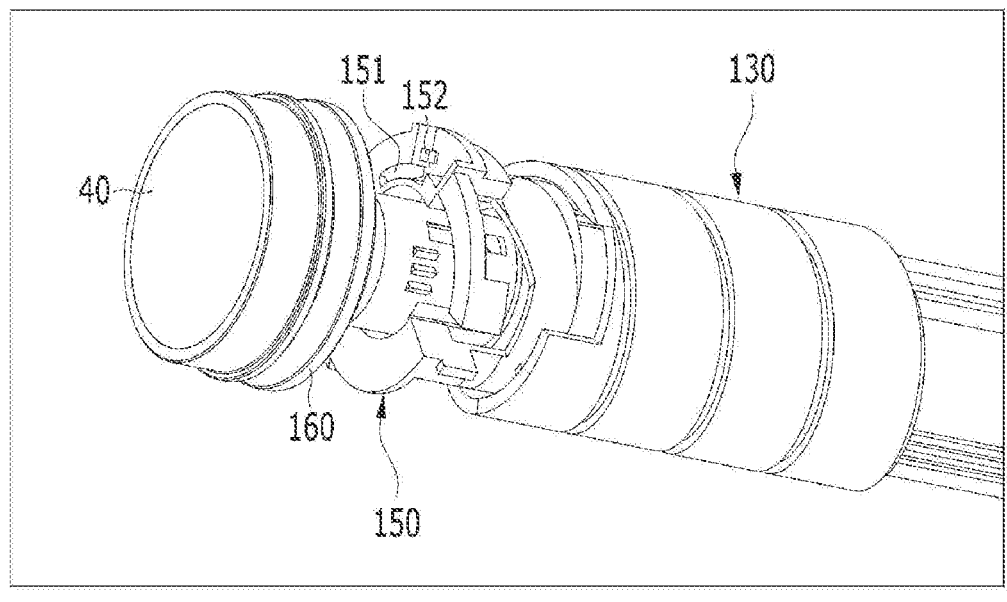
FIG. 6 shows an injection button, a button plate, a reset tube, a spring base and a scale drum assembled together.
Figure 7:
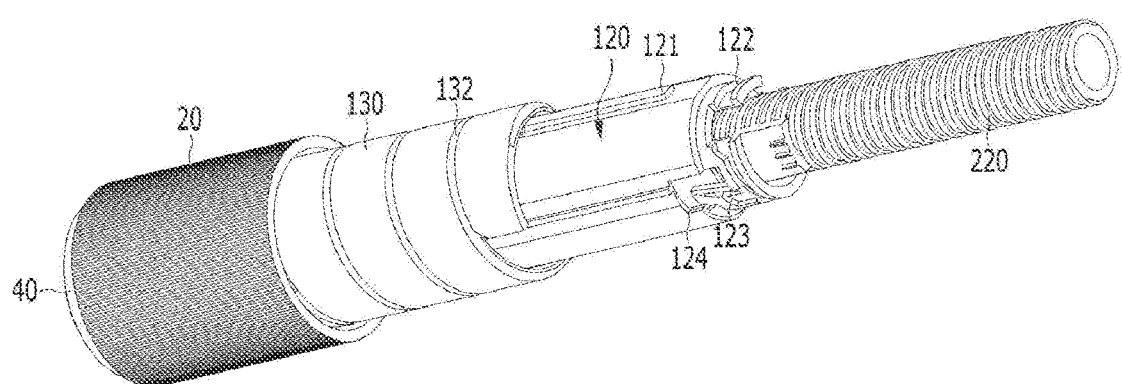
FIG. 7 shows a dose dial, a scale drum, a ratchet tube, a reset tube and a piston rod assembled together.

Hereinafter, the embodiments of the present disclosure will be described in more detail with reference to the accompanying drawings. However, the present disclosure is not limited to the following disclosed embodiments and will be embodied in a variety of different forms, and these embodiments are provided so that this disclosure will be thorough and complete, and will fully convey the scope of the present disclosure to those skilled in the art. In the drawings, like reference signs denote like elements.

In adding the reference signs to the elements in each drawing, it should be noted that like elements have like reference signs as possible although they are shown in different drawings. Additionally, in describing the present disclosure, when it is determined that a certain detailed description of relevant known elements or functions may obscure the subject matter of the present disclosure, its detailed description is omitted.

Hereinafter, a drug injection control device having a structure in which a rod guide 210 rotates and a piston rod moving with the rod guide 210 makes a linear motion to stably inject a drug set through a dose dial according to an embodiment of the present disclosure will be described with reference to FIGS. 1 to 10.

The drug injection control device includes a hollow housing 10, a dose dial 20 rotatably coupled to one side of the housing 10, a cartridge holder 30 fixedly coupled to the other side of the housing 10, wherein a cartridge containing a drug is received in the cartridge holder 30 and an injection needle is coupled to one side to deliver the drug, an injection button 40 positioned on the outer side of the dose dial 20, a button spring 50 to allow the injection button 40 to be pressed and restored in the dose dial 20, and a cap 60 separably coupled to the outside of the cartridge holder 30.

The present disclosure includes an injection amount setting module 100 configured to make a rotational motion with the dose dial 20 in the housing 10 to set an amount of drug to be injected by storing the twisting moment in a torsion spring; and a drug delivery module 200 switchably coupled to the injection amount setting module 100 by the operation of the injection button 40 to deliver the amount of drug set by the injection amount setting module 100 from the cartridge embedded in the cartridge holder 30 by moving through the release of the twisting moment applied to the torsion spring.

The injection amount setting module 100 includes a reset tube 110 switchably coupled to the dose dial 20 by the operation of the injection button 40, a ratchet tube 120 coupled to the outer side of the reset tube 110 to rotate at the same time, a scale drum 130 which slidably rotates along the axial direction on the outer surface of the ratchet tube 120, a torsion spring 140 having two ends coupled to the housing 10 and the ratchet tube 120, a spring base 150 to which the other side of the torsion spring 140 opposite to one side coupled to the ratchet tube 120 is fixed, a button plate 160 fixed and positioned in the dose dial 20 to perform the function of supporting the button spring 50, and an anchor 170 rotatably coupled to the ratchet tube 120 and slidably coupled to the inside of the housing 10.

The reset tube 110 is a structure having a hollow cylindrical shape, and includes a button coupling groove 111 formed along the circumferential direction on the outer circumferential surface for coupling of button legs 41 which constitute the injection button 40, a dial coupling protrusion 112 decouplably coupled to a tube coupling protrusion formed inside of the dose dial 20, and a tube coupling hole 113 coupled to the ratchet tube 120 to allow the ratchet tube 120 to rotate at the same time.

The ratchet tube 120 is a structure having a hollow cylindrical shape for receiving the reset tube 110 therein, and includes a drum guide protrusion 121 protruding along the lengthwise direction on the outer circumferential surface, an anchor coupling groove 122 formed along the circumferential direction to allow rotatable coupling of the anchor 170 on one side of the ratchet tube 120, a second tube coupling hole 123 connected to the first tube coupling hole of the reset tube 110, and a tube spring stop groove 124 which allows coupling with the end of the torsion spring 140.

The scale drum 130 includes a drum guide groove 131 formed along the lengthwise direction on the inner surface to match the drum guide protrusion formed in the ratchet tube 120, and a drum rotation groove 132 formed along a spiral shape on the outer circumferential surface to match a drum rotation protrusion protruding in a spiral shape on the inner surface of the housing 10.

The torsion spring 140 has two ends coupled to the spring base 150 and the ratchet tube 120, respectively, and during the rotation through the dose dial 20, one side 141 of the torsion spring 140 fixed to the ratchet tube 120 rotates, while the other side 142 of the torsion spring 140 fixed to the spring base 150 is kept in the fixed state, to get the spring twisted.

The spring base 150 is a structure which is positioned inside of the dose dial 20 and fixedly coupled to the housing 10 without movement, and includes a base spring stop groove 151 that allows coupling with the end of the torsion spring 140, and a ratchet 152 configured to generate a clicking sound when engaging with ratchet protrusions 22 formed in the dose dial 20 during the rotation of the dose dial 20. In other words, feedback on the injection amount is provided through the sequential contact between the ratchet and the ratchet protrusions 22 formed on one surface of a dial partition wall 21 formed on the inside of the dose dial 20 along the radial direction by rotating the dose dial 20.

The button plate 160 is in the shape of a circular plate fixed and positioned on a first chamber formed on one side with respect to the dial partition wall of the dose dial 20, and includes a guide fixing hole 161 formed at the center of the button plate 160 and a plurality of button guide holes 162 radially formed with respect to the guide fixing hole. The plurality of button legs 41 that constitutes the injection button 40 is coupled through the plurality of button guide holes. In other words, the button plate 160 allows a stable linear motion of the injection button 40 and stable placement of the button spring 50 on the injection button 40. The button spring 50 is placed on the button plate 160 and when the injection button 40 is pressed, the button spring 50 is compressed to the lowest point being the button plate 160, and when the pressure is removed, the button spring 50 restores its original state.

Figure 8:
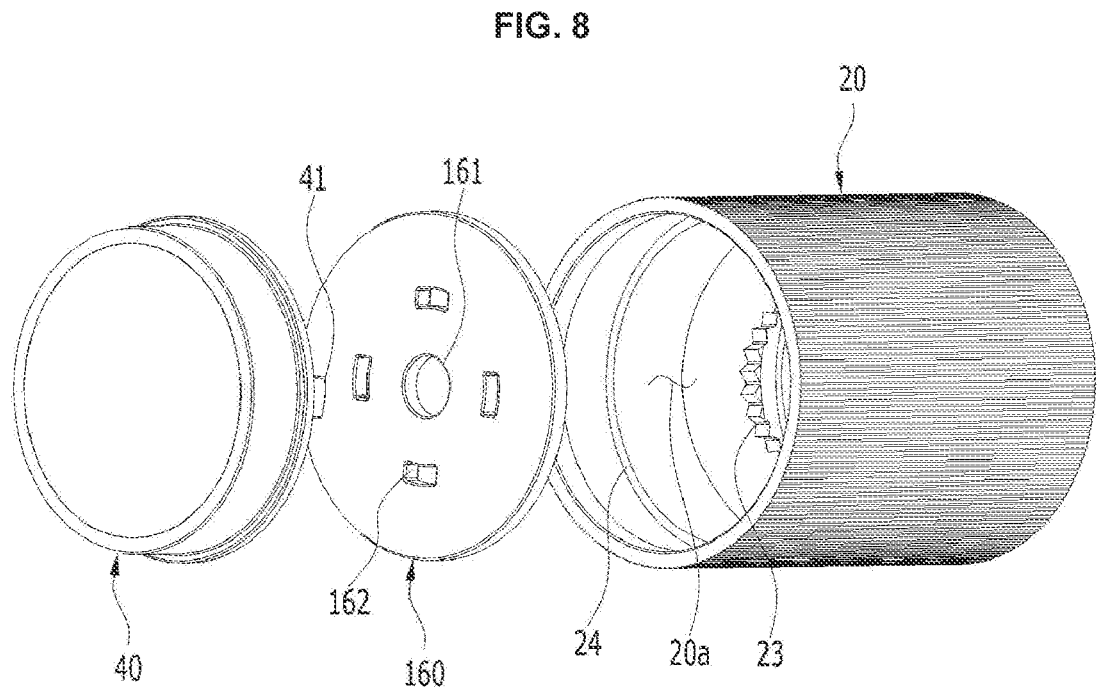
FIG. 8 shows an injection button, a button plate and a dose dial assembled together.
Figure 9:
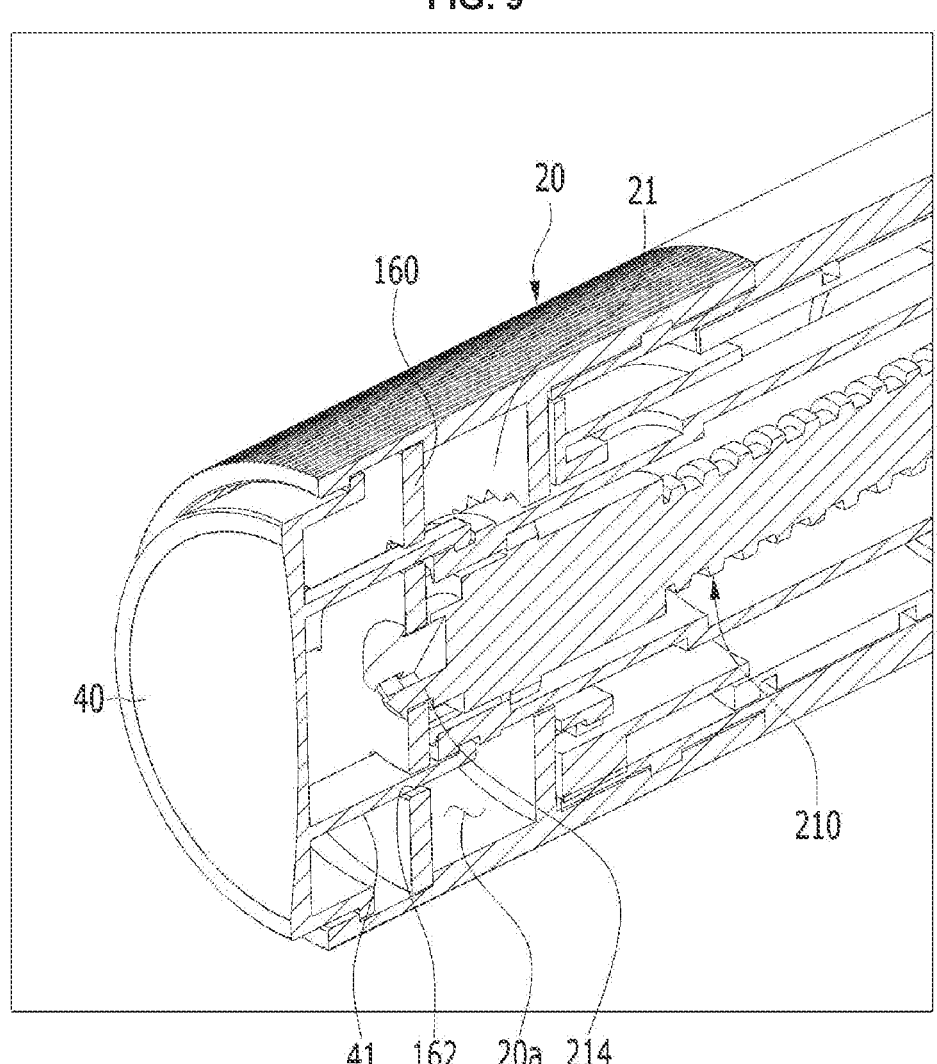
FIG. 9 is an enlarged view of section B in FIG. 3.
Figure 10:
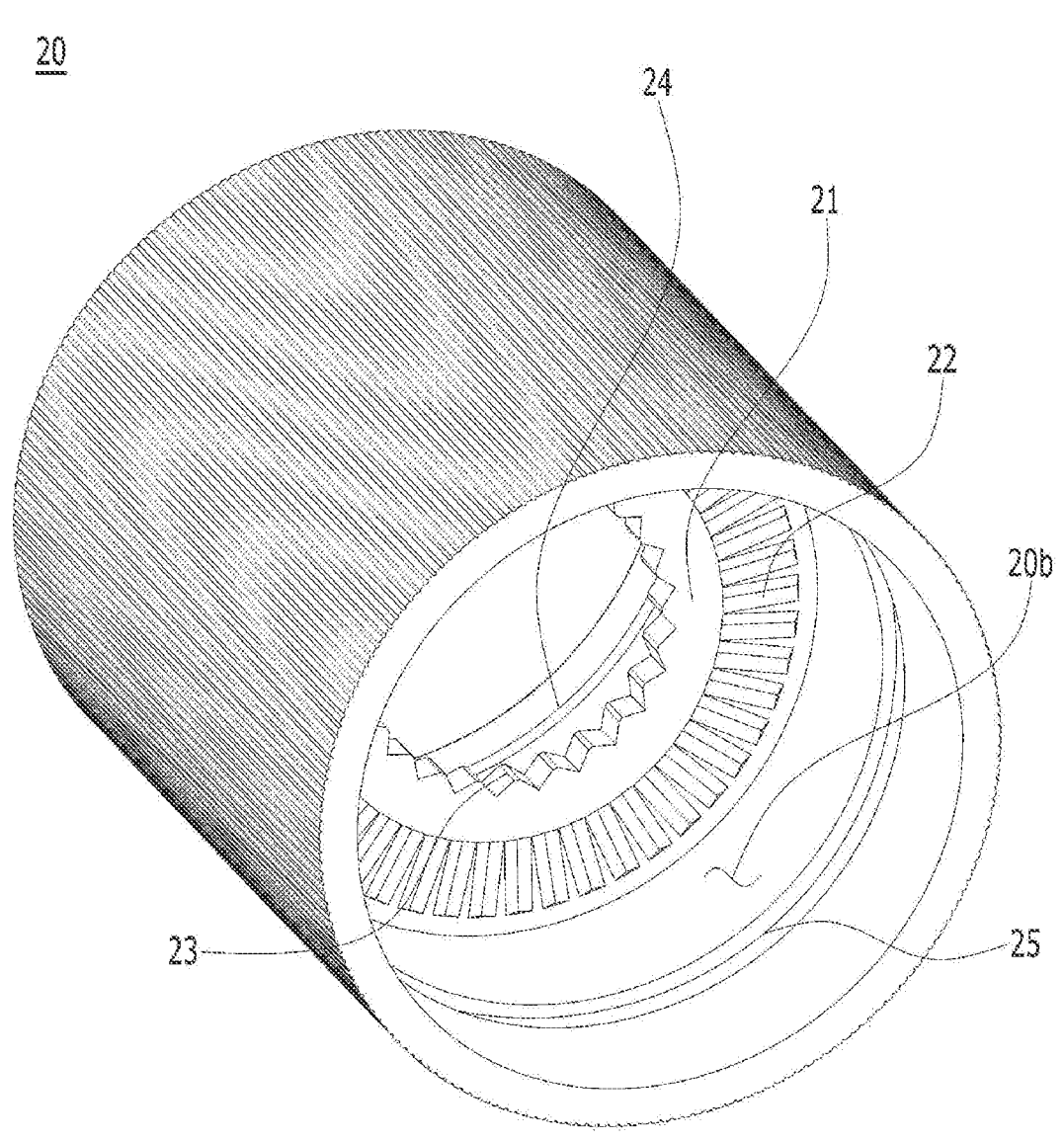
FIG. 10 shows a dose dial.

Referring to FIGS. 8 to 10, the button plate 160 is positioned on the first dial chamber 20a formed on one side with respect to the dial partition wall 21 formed in the dose dial 20, and the injection button 40 is slidably coupled through the plurality of button guide holes 162 formed in the button plate 160. The plurality of button guide holes 162 may be radially arranged at a predetermined distance with respect to the guide fixing hole 161. The plurality of button legs 41 has leg stop ends of a curved structure at the end to prevent the slip from the button guide holes 162.

The button plate 160 is fixed to a plate fixing step 24 formed along the circumferential direction on the inner surface of the dose dial 20 on the first dial chamber 20a.

In other words, the button plate 160 is coupled moveably with the rotation of the dose dial 20. In this state, the injection button 40 rotates simultaneously with the rotation of the dose dial 20, but allows a stable pushing motion through the button plate 160.

The anchor 170 includes an anchor circumferential protrusion 171 protruding along the circumferential direction on the inner surface and a housing coupling protrusion 172 formed along the axial direction on the outer circumferential surface. The anchor circumferential protrusion 171 is fitted into the anchor 170 coupling groove formed on the ratchet tube 120, and the housing coupling protrusion 172 is fitted into an anchor sliding portion 11 formed in the inner surface of the housing 10.

In the unpressed state of the injection button 40, the dose dial 20 is rotated as follows.

The reset tube 110 coupled to a tube coupling teeth formed along the circumferential direction on the inner surface of the dose dial 20 is coupled to the ratchet tube 120 coupled through the other side of the reset tube 110 and is coupled to the scale drum 130 slidably coupled along a drum guide rail positioned in a straight line shape along the axial direction on the outer surface of the ratchet tube 120, and the scale drum 130 is coupled to match a drum guide spiral protrusion spirally formed on the inner surface of the housing 10. Through this, as a consequence, the rotation of the dose dial 20 allows the scale drum 130 to move a predetermined distance along the housing 10 and storage of the twisting moment of the torsion spring 140.

The drug delivery module 200 includes the rod guide 210 switchably coupled to the reset tube 110 by the operation of the injection button 40, the piston rod 220 screw-coupled to the outer surface of the rod guide 210 to deliver the drug from the cartridge embedded in the cartridge holder 30 by making a linear motion with the rotational motion of the rod guide 210, a rod holder 230 coupled to the cartridge holder 30 and through which the piston rod 220 is coupled along the axial direction, and a rod lock 240 screw-coupled to the outer surface of the piston rod 220 in the rod holder 230.

The rod guide 210 includes a guide body 211 having a guide spiral protrusion 212 separably coupled to a guide coupling groove formed in the inner surface of the piston rod 220, a guide rotation protrusion 213 protruding on the outer surface of one side of the guide body and separably coupled to a guide coupling groove formed on the inner surface of the reset tube 110, and a guide ball 214 protruding along the axial direction at the end of the guide body and coupled to a guide fixing hole formed at the center of the button plate 160. In other words, when the rod guide 210 is in a rotatable state in place without vertical movement by the guide ball coupled through the guide fixing hole of the button plate 160 fixedly coupled to the dose dial 20, the rod guide 210 is switchably coupled to or decoupled from the reset tube 110 through the guide rotation protrusion, and allows a relative motion by screw coupling with the piston rod 220 through the guide spiral protrusion.

The piston rod 220 has a hollow cylindrical shape through which the rod guide 210 is coupled along the axial direction, and includes a rod movement portion 221 having a lock coupling protrusion to which the rod lock 240 is rotatably coupled and a rod stop portion 222 having a stop step 223 to stop the rod lock 240 from rotating.

The rod holder 230 has a hollow cylindrical shape, and is fixed to the outer side of the cartridge holder 30 through a holder fixing step 231 protruding along the circumferential direction on the outer circumferential surface, and allows a linear motion of the rod lock 240 through a lock guide 232 formed therethrough along the lengthwise direction on the outer circumferential surface.

The rod lock 240 is screw-coupled to the outer surface of the piston rod 220 to allow a rotational motion with the linear motion of the piston rod 220.

The rod lock 240 includes a lock body 241 coupled to the outer surface of the piston rod 220, and a lock protrusion 243 protruding along the axial direction on one side of the lock body. The lock protrusion makes a linear motion along the axial direction of the cartridge holder 30 when it is inserted into a lock guide 232. According to the above-described structure, the rod lock 240 moves with the rotation of the piston rod 220, but only can make a linear motion along the lock guide 232 under restricted rotation by the lock guide 232.

In the present disclosure, the rod guide is screw-coupled to the inside of the piston rod having the internal screw, and when the rod guide coupled to the reset tube is rotated in place with the rotation of the reset tube, the piston rod engaged with the rod guide is moved down to the cartridge holder.

The rod lock is rotatably connected to the external screw of the piston rod, and in this state, the rod holder is installed around the piston rod and the rod lock to allow the piston rod to rotate and the rod lock to make a linear motion.

When the injection button 40 operates, the rod guide 210 coupled to the reset tube 110 is connected to the inside of the piston rod 220 by screw rotation coupling to allow a sub-linear motion of the piston rod 220 through the rotation of the rod guide 210.

The drug injection control device according to the present disclosure as described above allows a structure in which the rod guide 210 rotates and the piston rod moving with the rod guide 210 makes a linear motion to stably inject the drug set through the dose dial.

The foregoing description is made to describe the technical spirit of the present disclosure for illustrative purposes, and it is obvious to those skilled in the art that a variety of modifications and change may be made thereto without departing from the essential features of the present disclosure. Therefore, the embodiments disclosed herein are provided to describe the technical spirit of the present disclosure and not intended to be limiting, and the technical spirit and scope of the present disclosure is not limited by the embodiments. The scope of protection of the present disclosure should be interpreted by the appended claims, and it should be interpreted that the scope of protection of the present disclosure covers all the technical spirit within the equivalent scope.

What is claimed is:

1. A drug injection control device comprising:
    a housing being hollow;
    a dose dial rotatably coupled to a side of the housing;
    a cartridge holder fixedly coupled to an opposite side of the housing, wherein a cartridge containing a drug is configured to be received in the cartridge holder and an injection needle is configured to be coupled to a side to deliver the drug;
    an injection button positioned on an outer side of the dose dial;
    a button spring configured to allow the injection button to be pressed and restored in the dose dial;
    a cap separably coupled to an outside of the cartridge holder;
    an injection amount setting module to set an amount of the drug to be injected by storing a twisting moment in a torsion spring positioned in the housing; and
    a drug delivery module to deliver the drug from the cartridge embedded in the cartridge holder by moving through the release of the twisting moment applied to the torsion spring, wherein the injection amount setting module includes a button plate fixed and positioned in the dose dial to perform a function of supporting the button spring,
    wherein the injection button is slidably coupled through the button plate, wherein the drug delivery module includes:
    a rod guide switchably coupled to the injection amount setting module by the operation of the injection button, and
    a piston rod screw-coupled to an outer side of the rod guide to deliver the drug from the cartridge embedded in the cartridge holder by making a linear motion with a rotational motion of the rod guide, and
    wherein the injection button rotates simultaneously with the rotation of the dose dial, but allows a stable pushing motion through the button plate,
    wherein the button plate is fixed to a plate fixing step formed along a circumferential direction on an inner surface of the dose dial on a first dial chamber formed through a partition wall in the dose dial;
    wherein the injection amount setting module includes a reset tube switchably coupled to the dose dial by the operation of the injection button, a ratchet tube coupled to an outer side of the reset tube to rotate at the same time, a scale drum which slidably rotates along an axial direction on an outer surface of the ratchet tube, and the spring having two ends coupled to the housing and the ratchet tube, and wherein the rod guide coupled to the reset tube is connected to an inside of the piston rod by screw rotation coupling to allow a sub-linear motion of the piston rod through the rotation of the rod guide, thereby having a cartridge drug release structure through the screw coupling between the piston rod and the rod guide.

2. The drug injection control device according to claim 1, wherein comprises a spring base coupled to the housing, and the torsion spring has two ends coupled to the spring base and the ratchet tube, respectively, and
    wherein during the rotation through the dose dial, a side of the torsion spring fixed to the ratchet tube rotates, while an opposite side of the torsion spring fixed to the spring base is kept in fixed state, to get the spring twisted.

3. The drug injection control device according to claim 1, wherein the button plate includes a guide fixing hole formed at a center of the button plate and a plurality of button guide holes radially formed with respect to the guide fixing hole.

4. The drug injection control device according to claim 1, wherein the injection button comprises a plurality of button legs respectively coupled through button guide holes of the button plate.

5. The drug injection control device according to claim 4, wherein the plurality of button legs have leg stop ends of a curved structure at the end to prevent slip from the button guide holes.

6. The drug injection control device according to claim 1, wherein the reset tube includes a button coupling groove formed along a circumferential direction on an outer circumferential surface for coupling of button legs.

7. The drug injection control device according to claim 1, wherein the rod guide includes a guide ball protruding along an axial direction at an end of a guide body and coupled to a guide fixing hole formed at the center of the button plate.

* * * * *